(12) United States Patent
Grellou et al.

(10) Patent No.: US 9,152,744 B2
(45) Date of Patent: Oct. 6, 2015

(54) METHODS, SYSTEMS, AND COMPUTER READABLE MEDIA FOR GENERATING A NON-DESTRUCTIVE INSPECTION MODEL FOR A COMPOSITE PART FROM A DESIGN MODEL OF THE COMPOSITE PART

(75) Inventors: Olivier Grellou, Villebrumier (FR); Sjoerd Van Der Veen, Tournefeuille (FR)

(73) Assignee: AIRBUS OPERATIONS (S.A.S.), Toulouse (FR)

( * ) Notice: Subject to any disclaimer, the term of this patent is extended or adjusted under 35 U.S.C. 154(b) by 328 days.

(21) Appl. No.: 13/434,394

(22) Filed: Mar. 29, 2012

(65) Prior Publication Data
US 2013/0262042 A1 Oct. 3, 2013

(51) Int. Cl.
*G06F 17/50* (2006.01)
*G06T 15/08* (2011.01)
*G01N 33/00* (2006.01)

(52) U.S. Cl.
CPC ........ *G06F 17/5009* (2013.01); *G06F 17/5095* (2013.01); *G01N 2033/0083* (2013.01); *G01N 2033/0096* (2013.01); *G06F 2217/46* (2013.01); *G06T 15/08* (2013.01)

(58) Field of Classification Search
CPC .................. G01N 29/4463; G01N 2021/8472; G01N 21/8851; G01N 2203/0298; G01N 2203/0664; G01N 2291/01; G01N 2291/011; G01N 2291/015; G01N 2291/2694; G01N 2291/044; G01N 29/265; G01N 29/225; G01N 2291/0231; G01N 29/043; G01N 2291/102; G01N 2291/106; G01N 29/07; G01N 29/221; G01N 29/2418; G01N 2033/0078; G01N 2033/0083; G01N 2033/0096; G06F 17/5009; G06F 2217/46
USPC ........ 703/1, 6; 73/618; 702/39, 113; 382/152
See application file for complete search history.

(56) References Cited

U.S. PATENT DOCUMENTS 5,381,518 A * 1/1995 Drebin et al. ................. 345/424
6,373,977 B1 * 4/2002 Culbertson ................... 382/154

(Continued)

OTHER PUBLICATIONS

Dominguez et al. Ultra-Fast Ultrasonic Inspection for Aeronautical Composites Using Paintbrush Acquisitions and Data Processing on GPU, 10th ECNDT 2010—European Conference on NDT, Moscow Jun. 7-11, 2010, Session: NDT of Transport Means teaches 3D modeling of aerospace composite parts where reconstructions are run only for probe positions for which.*

(Continued)

*Primary Examiner* — Mary C Jacob
*Assistant Examiner* — Scott S Cook
(74) *Attorney, Agent, or Firm* — Jenkins, Wilson, Taylor & Hunt, P.A.

(57) ABSTRACT

Methods, systems, and computer readable media for generating a nondestructive inspection model are provided, where such methods, systems and computer readable media are particularly suitable for use with aerospace parts or components. The method can include occurring at a computing platform with a memory and a processor, and analyzing, by the processor, a design model file stored in the memory to determine one or more properties of a composite part, the design model file describing one or more physical characteristics of the composite part. The method also can include generating, by the processor, a non-destructive inspection model for the composite part based on the one or more properties of the composite part determined by analyzing the design model file.

14 Claims, 7 Drawing Sheets

(56) References Cited

U.S. PATENT DOCUMENTS

| | | | |
|---|---|---|---|
| 6,765,570 B1* | 7/2004 | Cheung et al. | 345/420 |
| 6,867,774 B1* | 3/2005 | Halmshaw et al. | 345/424 |
| 7,218,323 B1* | 5/2007 | Halmshaw et al. | 345/424 |
| 7,483,818 B2* | 1/2009 | Amakai et al. | 703/1 |
| 7,965,290 B1* | 6/2011 | Kouznetsov et al. | 345/419 |
| 8,176,053 B2* | 5/2012 | Salemann | 707/741 |
| 2002/0113787 A1* | 8/2002 | Ray et al. | 345/424 |
| 2003/0052875 A1* | 3/2003 | Salomie | 345/419 |
| 2005/0168461 A1* | 8/2005 | Acosta et al. | 345/419 |
| 2006/0290695 A1* | 12/2006 | Salomie | 345/420 |
| 2007/0199381 A1* | 8/2007 | Volker | 73/625 |
| 2007/0229501 A1* | 10/2007 | Kouznetsov et al. | 345/424 |
| 2007/0244590 A1* | 10/2007 | Menayo et al. | 700/98 |
| 2008/0247636 A1* | 10/2008 | Davis et al. | 382/152 |
| 2009/0303233 A1* | 12/2009 | Lin et al. | 345/419 |
| 2011/0274369 A1* | 11/2011 | Smith et al. | 382/280 |
| 2014/0216158 A1* | 8/2014 | Sanabria Martin et al. | 73/588 |

OTHER PUBLICATIONS

Ledger, A., Deschamps, M., (eds) Ultrasonic Wave Propagation in Non Homogeneous Media ISSN 0930-8989, 2009 Springer-Verlag Berlind Heidelberg teaches modeling composites using ultrasonic data.*

Tanarro et al. Ultrasonic Inspection of Aerospace Parts: The Challenge of Working on the 3D World, May 13, 2008 downloaded from the internet http://www.ndt.net/article/wcndt00/papers/idn364/idn364.htm.*

Polytec News, InFocus Optical Measurement Solutions, Non-destructive Testing for Structural Health Monitoring, Reliability and Many Other Applications, Issue 02, 2011 teaches laser ultrasonic scanning for structural damage diagnosis on aerospace components on p. 6.*

Dominguez, N., Grello, O., Van-der-Veen, Simulation of Ultrasonic NDT in Composite Radius, 10th ECNDT 2010—European Conference on NDT, Moscow Jun. 7-11, 2010, Session: NDT of Transport Means.*

Smith, R.A., Nelson L.J., Automated Analysis and Advanced Defect Characterisation from Ultrasonic Scans of Composites, Journal of the British Institute of NDT, vol. 51(2), pp. 82-87, 2009.*

Cao, Z., Qin, D., Research on 3D Reconstruction for Automated Ultrasonic Inspection System, Proceedings of the 2009 IEEE International Conference on Mechatronics and Automation, Aug. 9-12, Changchun China.*

LeGault, M.R., Aircraft Simulation Gets Composites Aware, Feb. 23, 2009 http://www.compositesworld.com/articles/aircraft-simulation-gets-composites-aware.*

Keulen, J.V., Density of Porous Solids, vol. 6—No. 33—1973 Materiaux et Construction.*

Joseph O'Rourke, "Finding minimal enclosing boxes," Parallel Programing, Springer Netherlands, 1985.

* cited by examiner

FIG. 1

Photograph of CFRP stiffener radius

METHODS, SYSTEMS, AND COMPUTER READABLE MEDIA FOR GENERATING A NON-DESTRUCTIVE INSPECTION MODEL FOR A COMPOSITE PART FROM A DESIGN MODEL OF THE COMPOSITE PART

TECHNICAL FIELD

The subject matter described herein relates generally to generating a non-destructive inspection model for a composite part from a design model of the composite part. More particularly, the subject matter disclosed herein relates to methods, systems, and computer readable media for generating a non-destructive inspection model for a composite part from a design model of the composite part where such methods, systems and computer readable media are particularly suitable for use, for example and without limitation, with aerospace parts or components.

BACKGROUND

Composite parts are often subjected to high stress environments. For example, many aerospace applications employ composite parts (e.g., parts containing carbon fiber reinforced polymer (CFRP) and/or graphite fiber reinforced polymer (GFRP)) where strength, durability, and weight are determinative factors. It is therefore often important to periodically subject composite parts to inspection. Once installed, however, physical internal inspection of a composite part might require destruction of the part itself. Various technological advances, for example in the use of acoustic waves, support non-destructive inspection of composite parts.

Non-destructive inspection of a composite part involves the development of a model for the composite part that predicts expected results, for example, responses from a given acoustic wave. Once a model for a composite part is developed, analogous testing may be performed on installed counterpart parts, and the results compared with the model's predicted results.

Generating a non-destructive inspection model for a composite part is often a complex, tedious, and resource intensive endeavor that requires determining one or more properties of the composite part for which a model is being developed. Modern composite parts, however, are often designed using design modeling tools (e.g., computer aided design (CAD) systems) that produce rich descriptions of the composite parts.

Accordingly, a need exists for methods, systems, and computer readable media for generating a non-destructive inspection model for a composite part from a design model of the composite part.

SUMMARY

According to one aspect, the subject matter described herein can comprise a method for generating a non-destructive inspection model for a composite part from a design model of the composite part. The method can comprise steps occurring at a computing platform including a memory and a processor. The steps can include analyzing, by the processor, a design model file stored in the memory to determine one or more properties of a composite part, the design model file describing one or more physical characteristics of the composite part. The steps also can include generating, by the processor, a non-destructive inspection model for the composite part based on the one or more properties of the composite part determined by analyzing the design model file.

According to another aspect, the subject matter described herein can include a system for generating a non-destructive inspection model from a design model. The system can include a processor and can include a memory. The system further can include a design file analysis module configured to analyze a design model file to determine one or more properties of a composite part, the design model file describing one or more physical characteristics of the composite part. The system further can include a non-destructive inspection model generation module configured to generate a non-destructive inspection model for the composite part based on the one or more properties of the composite part determined by analyzing the design model file.

As used herein, the term "module" refers to software in combination with hardware (such as a processor) and/or firmware for implementing features described herein.

The subject matter described herein can be implemented in software in combination with hardware and/or firmware. For example, the subject matter described herein may be implemented in software executed by one or more processors. In one exemplary implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein can include non-transitory computer readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which.

DETAILED DESCRIPTION

Methods, systems, and computer readable media for generating a non-destructive inspection model for a composite part from a design model of the composite part are provided. The methods, systems and computer readable media described herein are particularly suitable, for example and without limitation, with aerospace parts or components. As used herein, aerospace includes any type or aircraft or spacecraft. As noted above, many aerospace applications employ composite parts (e.g., parts containing carbon fiber reinforced polymer (CFRP) and/or graphite fiber reinforced polymer (GFRP)) where strength, durability, and weight may be important factors to determine, evaluate and/or monitor. For example and without limitation, composite parts have been utilized in the construction of many types of aerospace structures, including aerospace wing ailerons, wing outerflaps, wing j-noses, wing spoilers, wing ribs, vertical tail planes, horizontal tail planes, rear pressure bulkheads, floor panels, center wing boxes, landing gear doors, fuselages, radomes, and/or floor beams.

Significant progress has been made in modeling the propagation of acoustic waves in complex mediums. Because an acoustic wave is mechanical, its propagation depends on the medium in which it propagates. Thus, developing an accurate model for the propagation of an acoustic wave in a complex medium requires an understanding of the physical internal representation of the medium being modeled. For example, the model may depend on the density of the medium (e.g., concerning the CFRP/GFRP ply and/or resin), the speed of the acoustic wave in the medium (e.g., concerning the CFRP/GFRP ply and/or resin), the orientation of the medium (e.g., concerning the CFRP/GFRP ply and/or resin), the layup law (i.e., order) of the medium, and/or interply data describing the medium.

Manually developing a physical internal description of a medium, however, is a time consuming task that is not guaranteed to produce an efficient representation. Meanwhile, many composite parts constructed from complex mediums are designed using design modeling tools (e.g., CAD systems) that produce rich descriptions of the composite parts. These rich descriptions or design model files often contain sufficient data for developing the physical internal description necessary to generate a non-destructive inspection model. As described in greater detail below, and in accordance with embodiments of the subject matter described herein, a non-destructive inspection model for a composite part may be generated from a design model of the composite part. While composite parts are often employed in aerospace and aircraft applications, it will be appreciated by those having ordinary skill in the art, that the subject matter described herein may be utilized to generate a non-destructive inspection model for any type of composite part regardless of its application.

Figure 1:
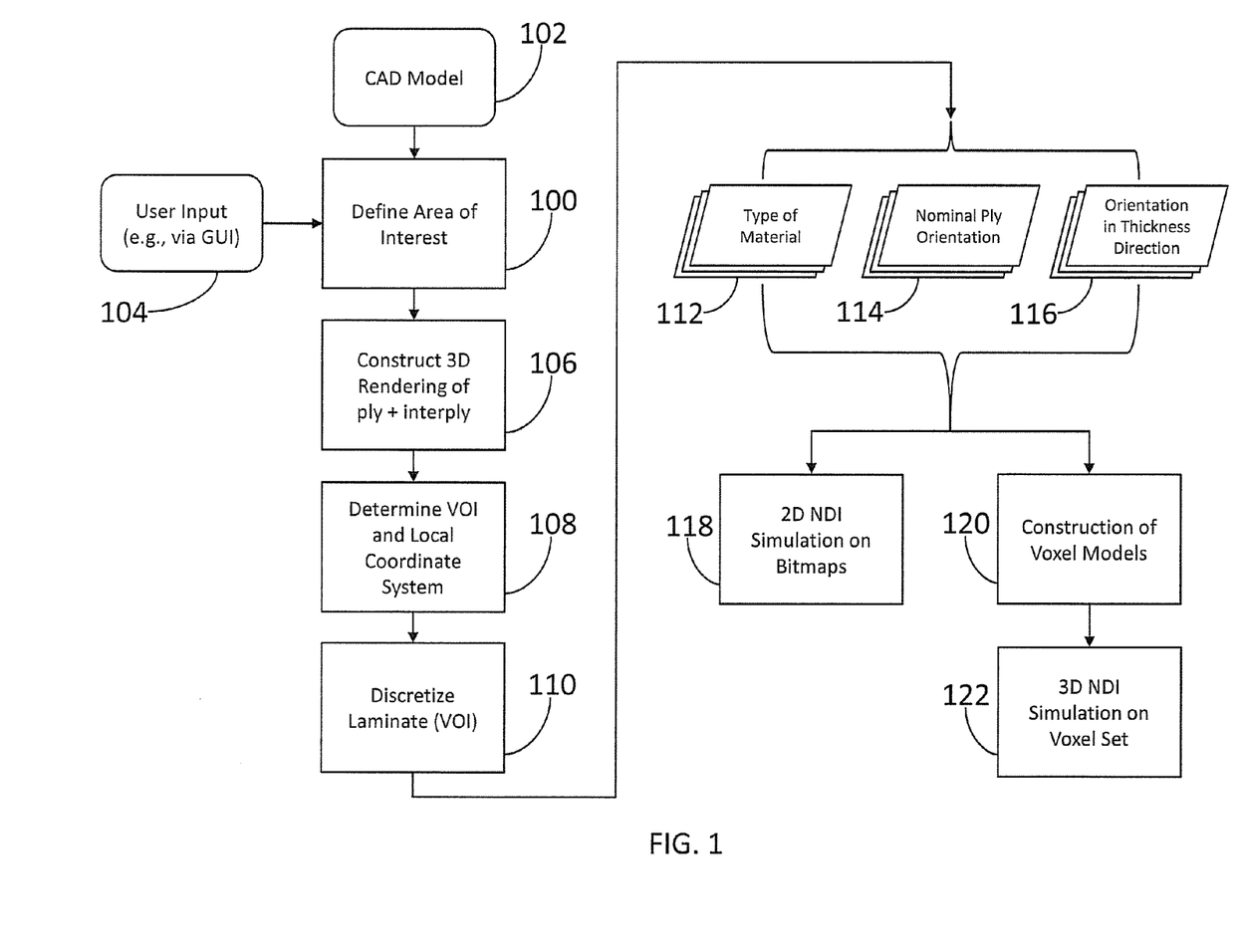
FIG. 1 is a flow chart illustrating an exemplary sequence for generating a non-destructive inspection model for a composite part from a design model of the composite part in accordance with aspects of the subject matter described herein.
Figure 2:
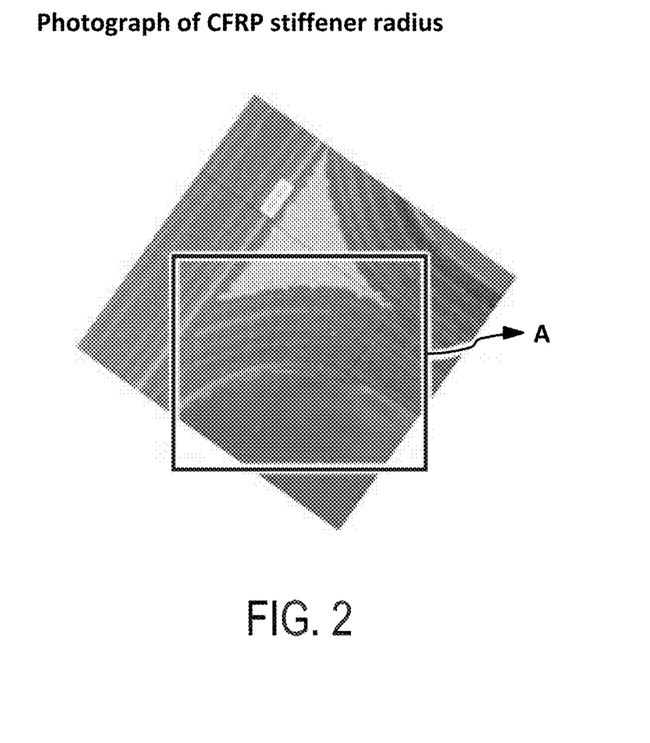
FIG. 2 is a photograph illustrating the stiffener radius of a CFRP composite part for which a non-destructive inspection model may be generated from a design model in accordance with aspects of the subject matter described herein.

FIG. 1 is a flow chart illustrating an example of a sequence for generating a non-destructive inspection model for a composite part from a design model of the composite part in accordance with embodiments of the subject matter described herein. Referring to FIG. 1, in step 100, an area of interest (AOI) may be defined within design model file 102, based on user input 104. For example, design model file 102 may be a CAD file created by a user that describes the composite part's geometry and/or material lay-up. User input 104 may be captured by the CAD system, for example, using "sketch-and-project" functionality. For example, a user may utilize "sketch-and-project" functionality provided by the CAD system to sketch a rectangle delimiting an AOI for non-destructive inspection simulation, and the CAD system may project the rectangle on the composite part described by design model file 102. The selected AOI may then be "cut out" perpendicular to the local surface normal (i.e., "local Z axis") to ensure a sufficient thickness representation. For example, FIG. 2 is a photograph illustrating the stiffener radius of a CFRP composite part for which a non-destructive inspection model may be generated from a design model in accordance with embodiments of the subject matter described herein. A portion of FIG. 2 is denoted as A, where a close up view of A can be seen in FIG. 4. As described previously, the composite part or portion can be, but is not limited to being, an aerospace component or part or any other suitable component or part where strength, durability, and/or weight may be factors to be evaluated or monitored. For example and without limitation, the composite part may be at least a portion of an aerospace wing aileron, wing outerflap, wing j-nose, wing spoiler, wing rib, vertical tail plane, horizontal tail plane, rear pressure bulkhead, floor panel, center wing box, landing gear door, fuselage, radome, and/or floor beam. Returning to FIG. 1, at step 106, a three-dimensional (3D) rendering may be constructed which indicates ply and interply information for the AOI While many CAD systems do not display the composite lay-up, it is generally possible to produce a detailed rendering showing each ply and thickness transition. For example, user input 104 may include a parameter corresponding to interply thickness which may be utilized to enhance the rendering. Similarly, user input 104 may include additional parameters which may be utilized in generating a non-destructive inspection model. For example, user input 104 may include one or more material properties (e.g., density and/or stiffness of the interplies) of the composite part which may be useful in generating a non-destructive inspection model for the composite part (e.g., interply density may affect a simulated ultrasound propagation). The rendering may be further enhanced to include additional salient features (e.g., interplies, Zpins, and/or through-thickness reinforcements). For example, if the composite part includes Z-pins, user input 104 may include information describing the size, location, and/or material of Z-pins relevant to the simulation, and such information may subsequently be utilized to superimpose the Z-pins onto corresponding bitmap images. The inclusion of interply thickness in the rendering may be useful for generating an accurate non-destructive inspection model, as modern composite materials often employ an interply of significant thickness, leading to attenuation of inspection signals and/or otherwise interfering with propagation of ultrasound.

Figure 3:
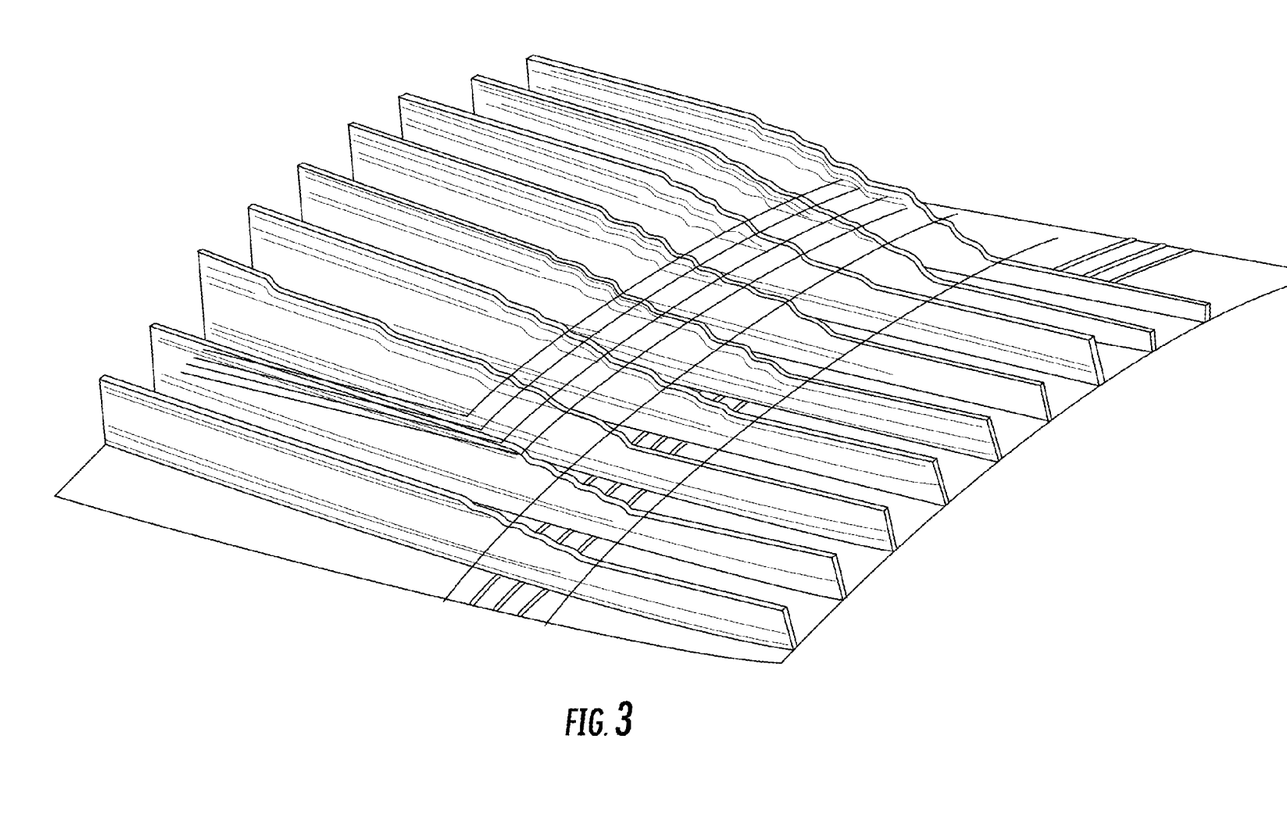
FIG. 3 is a screenshot illustrating a CAD model for a composite part including a series of cross sections from which a non-destructive inspection model may be generated in accordance with aspects of the subject matter described herein.

In step 108, a volume of interest (VOI) and local coordinate system corresponding to the AOI may be determined. For example, an arbitrarily oriented minimum bounding box may be defined around all material contained within the AOI. Defining such a minimum bounding box is a known minimization problem and algorithms to solve such a problem already exist. (See, for example, Joseph O'Rourke, "Finding minimal enclosing boxes," *Parallel Programing* (Springer Netherlands, 1985)). A local coordinate system for subsequent discretization by slicing may be determined from the orientation of the minimum bounding box, with the VOI being sectioned along the thickness direction of the minimum bounding box. In step 110, laminate within the VOI may be discretized into a voxel model. For example, FIG. 3 is a screenshot illustrating a CAD model for a composite part that includes a series of cross sections from which a non-destructive inspection model may be generated in accordance with embodiments of the subject matter described herein. Returning to FIG. 1, three series of cross section bitmaps 112, 114, and 116 may be generated. In order to make solving of the ultrasound propagation problem unconditionally stable, the non-destructive inspection simulation may require that pixel- or voxel-fineness=non-destructive inspection wavelength/10. This may translate to approximately 0.015×0.015 (×0.015) mm, and such cross section bitmaps may therefore be generated every 0.015 mm, with the resolution of each bitmap such that each pixel measures at most 0.015 mm×0.015 mm. Cross section bitmap series 112 may contain material information, for example, values (e.g., gray scale or color coded values) indicating the type of material (e.g., ply or interply, and/or of which material).

Cross section bitmap series 114 and 116 may contain discretized material orientation information in the local coordinate system of the minimum bounding box. For example, cross section bitmap series 114 may indicate nominal ply orientation (i.e., in-plane direction), by containing values (e.g., gray scale or color coded values) indicating the nominal direction of the plane in question (e.g., 0°, 45°, or any other possible design ply angle). Nominal ply orientations are generally available from the design model file, but in many modern composite parts (e.g., double-curved aerospace parts) the real ply orientation may differ significantly from the nominal direction locally, for example, due to shearing of the fabric during lay-up. Therefore, in some embodiments, orientations may be computed using a detailed composite lay-up simulation. Such a simulation may be run by the user before beginning the process of generating the non-destructive inspection model, with the results being used as an input when the non-destructive inspection model is generated. In such embodiments, the computed local material orientation may be translated into the coordinate system of the VOI and its minimum bounding box and then assigned a nominal direction value within bitmap series 114. Cross section bitmap series 116 may indicate orientation in thickness (i.e., out-of-plane direction), by containing values (e.g., gray scale or color coded values) indicating the orientation in thickness of the plane in question. Information pertaining to orientation in thickness, while generally not directly available from the design model file, may be computed from a detailed composite lay-up simulation, as described above with respect to nominal orientations. As with nominal orientations derived from a detailed composite lay-up simulation, the orientation in thickness values derived from the detailed composite lay-up simulation may be translated into the coordinate system of the VOI and its minimum bounding box and then assigned an orientation in thickness value within bitmap series 116.

Each of cross section bitmap series 112, 114, and 116 may use an identical sequential rank number in the filename of each bitmap. For example, one of the corners of the minimum bounding box may be chosen as an origin for the local coordinate system, and the bitmaps corresponding to this origin numbered "1" (e.g., <filename>_1.bmp), with subsequent cross sections receiving increasing rank numbers (e.g., the next cross section 0.015 mm away receiving rank number "2"). Thus bitmap series 112, 114, and 116 are sufficient to later construct a voxel model in a local coordinate system, with the pixel at the bottom-left of the bitmap (e.g., <filename>_1.bmp) serving as the origin and defining the voxel spanning 0.015×0.015×0.015 mm$^3$ in the positive octant.

Figure 4:
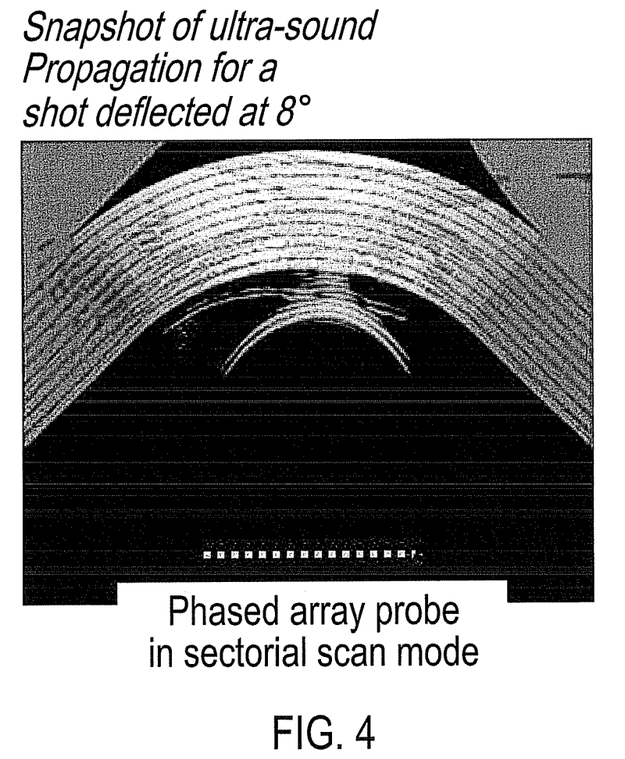
FIG. 4 is a close up view of a portion of the CFRP composite part of FIG. 2 illustrating a snapshot image taken by a phased array probe operating in section scan mode of an ultra-sound propagation for a shot deflected at eight degrees.
Figure 5:
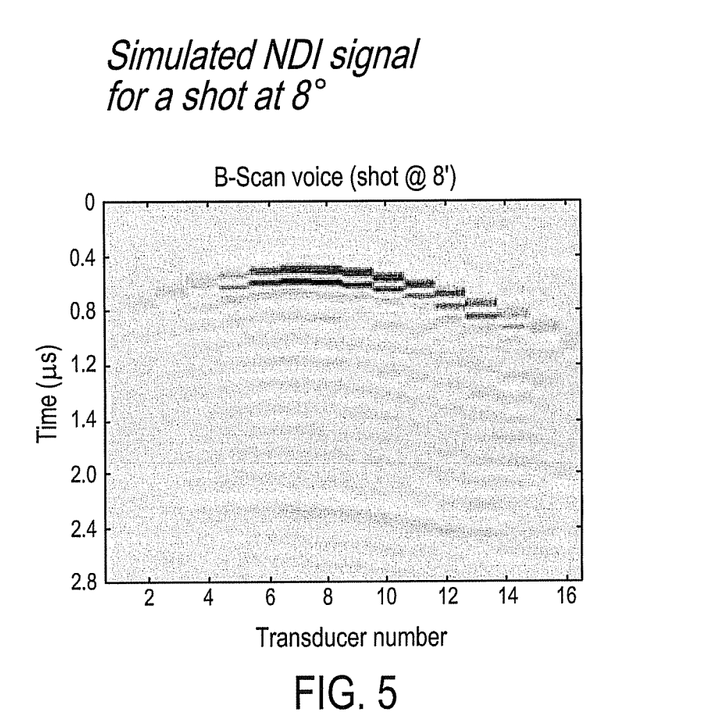
FIG. 5 is a screenshot illustrating a simulated non-destructive inspection signal for an ultra-sound propagation shot deflected from a composite part at eight degrees.

In step 118, cross section bitmap series 112, 114, and 116 may be used to perform two-dimensional (2D) non-destructive inspection simulations. For example, FIG. 4 is a close up view of portion A of the CFRP composite part of FIG. 2 illustrating a snapshot image taken by a phased array probe operating in section scan mode of an ultra-sound propagation for a shot deflected at eight degrees. Returning to FIG. 1, as discussed above, in step 120, a set of voxel models (e.g., three color-coded voxel models) for use in 3D non-destructive inspection simulation may be constructed from cross section bitmap series 112,114, and 116, for example, by extruding cross section bitmap series 112, 114, and 116, starting with the first bitmap in rank, and then moving to the second bitmap in rank, etc. The set of voxel models having been generated, in step 122, non-destructive inspection simulation may be performed on the voxel models. For example, FIG. 5 is a screenshot illustrating a simulated non-destructive inspection signal for an ultra-sound propagation shot deflected from a composite part at eight degrees.

Figure 6:
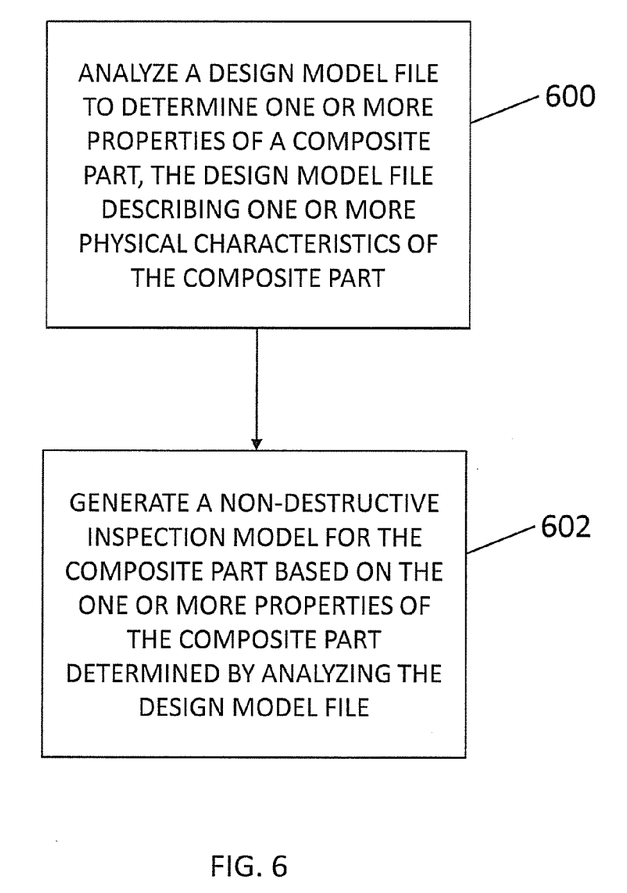
FIG. 6 is a flow chart illustrating an exemplary process for generating a non-destructive inspection model for a composite part from a design model of the composite part in accordance with aspects of the subject matter described herein.

FIG. 6 is a flow chart illustrating an exemplary process for generating a non-destructive inspection model for a composite part from a design model of the composite part in accordance with embodiments of the subject matter described herein. Referring to FIG. 6, in step 600, a design model file can be analyzed to determine one or more properties of a composite part, where the design model file can describe one or more physical characteristics of the composite part. For example, a design model file for a composite part may be analyzed to determine a ply and interply description for the composite part. In step 602, a non-destructive inspection model for the composite part is generated based on the one or more properties of the composite part determined by analyzing the design model file. For example, a non-destructive inspection model for the composite part may be generated based on the determined ply and interply description.

Figure 7:
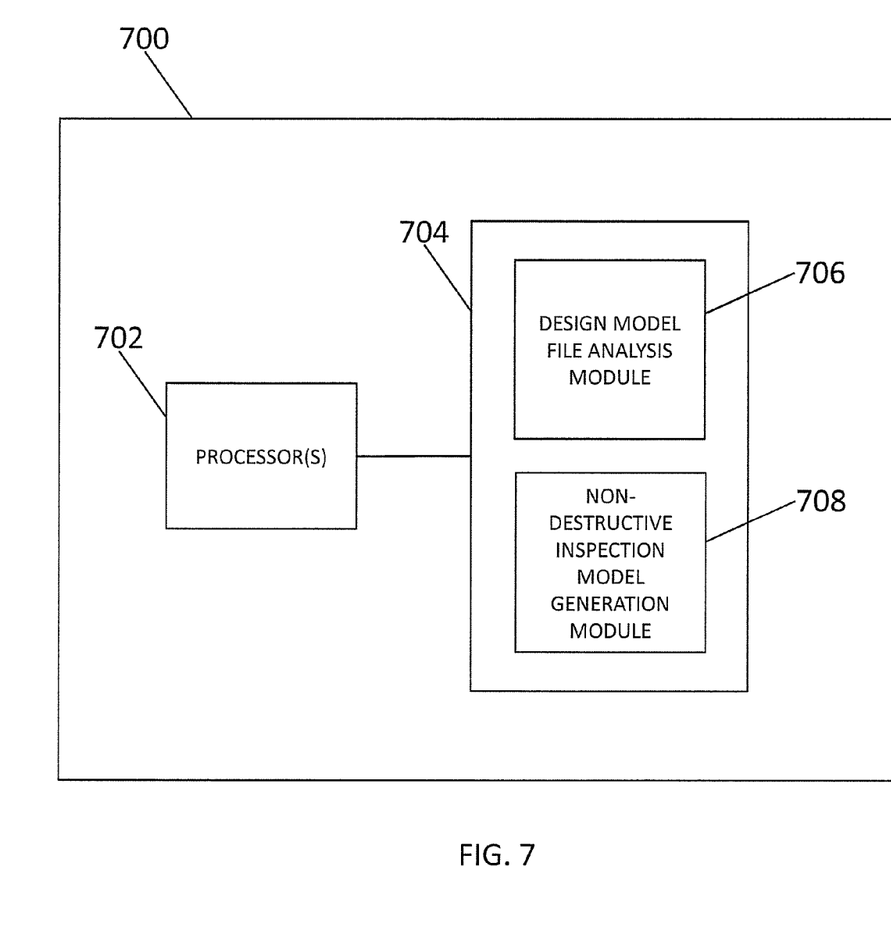
FIG. 7 is a block diagram illustrating an exemplary system for generating a non-destructive inspection model for a composite part from a design model of the composite part in accordance with aspects of the subject matter described herein.

FIG. 7 is a block diagram illustrating an exemplary system for generating a non-destructive inspection model for a composite part from a design model of the composite part in accordance with embodiments of the subject matter described herein. Referring to FIG. 7, system 700 can comprise a processor 702 and memory 704. Memory 704 may contain one or more modules for execution by processor 702. For example, memory 704 may contain design model file analysis module 706, which may be configured to analyze a design model file to determine one or more properties of a composite part, where the design model file can describe one or more physical characteristics of the composite part. For example, design model file analysis module 706 may be configured to analyze a design module file to determine a ply and interply description for the composite part. Memory 704 may also contain non-destructive inspection model generation module 708, which may be configured to generate a non-destructive inspection model for the composite part based on the one or more properties of the composite part determined by analyzing the design model file. For example, non-destructive inspection model generation module 708 may be configured to generate a non-destructive inspection model for the composite part based on the ply and interply description of the composite part.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for generating at a computing platform, including a memory and a processor, a non-destructive inspection model for a composite part from a design model of the composite part, the method comprising:

analyzing, by the processor, a design model file stored in the memory to determine a plurality of properties of the composite part, the design model file describing one or more physical characteristics of the composite part and comprising a computer aided design (CAD) model file for the composite part;

analyzing an area of interest of the CAD model file corresponding to a region of the composite part selected by a user;

generating, by the processor, a non-destructive inspection model for the composite part based on the plurality of properties of the composite part determined by analyzing the CAD model file by converting the area of interest into a volume of interest by formulating an arbitrarily oriented minimum bounding box that encompasses voxels corresponding to material contained within the area of interest; and constructing a set of voxel models from cross section bitmaps of the composite part, by extruding the cross section bitmaps, such that non-destructive inspection simulation is performed on the set of voxel models;

wherein the composite part comprises a portion of an aerospace component comprising at least one of carbon fiber reinforced polymer (CFRP) and/or graphite fiber reinforced polymer (GFRP); and wherein the plurality of determined properties of the composite part comprise at least one of a density of the composite part, a speed of a given acoustic wave in the composite part, an orientation of plies for the composite part, a layer layup rule for the composite part, a layer layup order for the composite part, a description of layer interply for the composite part, and an overall geometry for the composite part.

2. The method of claim 1 wherein generating the non-destructive inspection model for the composite part based on the plurality of properties of the composite part determined by analyzing the CAD model file comprises utilizing the plurality of properties of the composite part determined by analyzing the CAD model file and a user-inputted interply thickness parameter to construct a three-dimensional rendering of the composite part indicating ply of the composite part and interply of the composite part.

3. The method of claim 2 wherein generating the non-destructive inspection model for the composite part based on the plurality of properties of the composite part determined by analyzing the CAD model file comprises discretizing the three-dimensional rendering of the composite part into a voxel model comprising three cross section bitmaps of the composite part.

4. The method of claim 3 wherein a first of the three cross section bitmaps comprises pixels having values corresponding to material type and either ply or interply, a second of the three cross section bitmaps comprises pixels having values corresponding to nominal ply direction, and a third of the three cross section bitmaps comprises pixels having values corresponding to orientation in thickness.

5. The method of claim 1 wherein the composite part comprises at least a portion of at least an aerospace wing aileron, wing outerflap, wing j-nose, wing spoiler, wing rib, vertical tail plane, horizontal tail plane, rear pressure bulkhead, floor panel, center wing box, landing gear door, fuselage, radome, and/or floor beam.

6. A system for generating a non-destructive inspection model from a design model, the system comprising:
a processor;
a memory;
a design model file analysis module configured to analyze a design model file to determine a plurality of properties of a composite part, the design model file describing one or more physical characteristics of the composite part and comprising a computer aided design (CAD) model file for the composite part, and configured to analyze an area of interest of the CAD model file corresponding to a region of the composite part selected by a user; and a non-destructive inspection model generation module configured to generate a non-destructive inspection model for the composite part based on the plurality of properties of the composite part determined by analyzing the CAD model file by converting the area of interest into a volume of interest by formulating an arbitrarily oriented minimum bounding box that encompasses voxels corresponding to material contained within the area of interest, and to construct a set of voxel models from cross section bitmaps of the composite part, by extruding the cross section bitmaps, such that non-destructive inspection simulation is performed on the set of voxel models;

wherein the composite part comprises a portion of an aerospace component comprising at least one of carbon fiber reinforced polymer (CFRP) and/or graphite fiber reinforced polymer (GFRP); and wherein the plurality of determined properties of the composite part comprise at least one of a density of the composite part, a speed of a given acoustic wave in the composite part, an orientation of plies for the composite part, a layer layup rule for the composite part, a layer layup order for the composite part, a description of layer interply for the composite part, and an overall geometry for the composite part.

7. The system of claim 6 wherein the non-destructive inspection model generation module is configured to generate the non-destructive inspection model for the composite part based on the plurality of properties of the composite part determined by analyzing the CAD model file by utilizing the plurality of properties of the composite part determined by analyzing the CAD model file and a user-inputted interply thickness parameter to construct a three-dimensional rendering of the composite part indicating ply of the composite part and interply of the composite part.

8. The system of claim 7 wherein the non-destructive inspection model generation module is configured to generate the non-destructive inspection model for the composite part based on the plurality of properties of the composite part determined by analyzing the CAD model file by discretizing the three-dimensional rendering of the composite part into a voxel model comprising three cross section bitmaps of the composite part.

9. The system of claim 8 wherein a first of the three cross section bitmaps comprises pixels having values corresponding to material type and either ply or interply, a second of the three cross section bitmaps comprises pixels having values corresponding to nominal ply direction, and a third of the three cross section bitmaps comprises pixels having values corresponding to orientation in thickness.

10. The system of claim 6 wherein the composite part comprises at least a portion of an aerospace component.

11. The system of claim 10 wherein the composite part comprises at least a portion of at least an aerospace wing aileron, wing outerflap, wing j-nose, wing spoiler, wing rib, vertical tail plane, horizontal tail plane, rear pressure bulkhead, floor panel, center wing box, landing gear door, fuselage, radome, and/or floor beam.

12. A non-transitory computer readable medium comprising computer executable instructions that when executed by a processor of a computer control the computer to perform at a computing platform including a memory and the processor a method, the method comprising:

analyzing, by the processor, a design model file stored in the memory to determine a plurality of properties of a composite part, the design model file describing one or more physical characteristics of the composite part and comprising a computer aided design (CAD) model file for the composite part;

analyzing an area of interest of the CAD model file corresponding to a region of the composite part selected by a user;

generating, by the processor, a non-destructive inspection model for the composite part based on the plurality of properties of the composite part determined by analyzing the CAD model file by converting the area of interest into a volume of interest by formulating an arbitrarily oriented minimum bounding box that encompasses voxels corresponding to material contained within the area of interest; and     constructing a set of voxel models from cross section bitmaps of the composite part, by extruding the cross section bitmaps, such that non-destructive inspection simulation is performed on the set of voxel models;

wherein the composite part comprises a portion of an aerospace component comprising at least one of carbon fiber reinforced polymer (CFRP) and/or graphite fiber reinforced polymer (GFRP); and     wherein the plurality of determined properties of the composite part comprise at least one of a density of the composite part, a speed of a given acoustic wave in the composite part, an orientation of plies for the composite part, a layer layup rule for the composite part, a layer layup order for the composite part, a description of layer interply for the composite part, and an overall geometry for the composite part.

13. The non-transitory computer readable medium of claim 12 wherein the composite part comprises at least a portion of at least an aerospace wing aileron, wing outerflap, wing j-nose, wing spoiler, wing rib, vertical tail plane, horizontal tail plane, rear pressure bulkhead, floor panel, center wing box, landing gear door, fuselage, radome, and/or floor beam.

14. A method for generating at a computing platform, including a memory and a processor, a non-destructive inspection model for a composite part from a design model of the composite part, the method comprising:

analyzing, by the processor, a design model file stored in the memory to determine a plurality of properties of the composite part, the design model file describing one or more physical characteristics of the composite part and comprising a computer aided design (CAD) model file for the composite part;

analyzing an area of interest of the CAD model file corresponding to a region of the composite part selected by a user;

receiving a user-inputted interply thickness parameter;

generating, by the processor, a non-destructive inspection model for the composite part based on the plurality of properties of the composite part determined by analyzing the CAD model file and the user-inputted interply thickness parameter by converting the area of interest into a volume of interest by formulating an arbitrarily oriented minimum bounding box that encompasses voxels corresponding to material contained within the area of interest; and     constructing a set of voxel models from cross section bitmaps of the composite part, by extruding the cross section bitmaps, such that non-destructive inspection simulation is performed on the set of voxel models;

wherein the composite part comprises a portion of an aerospace component comprising at least one of carbon fiber reinforced polymer (CFRP) and/or graphite fiber reinforced polymer (GFRP); and     wherein the plurality of determined properties of the composite part comprise at least one of a density of the composite part, a speed of a given acoustic wave in the composite part, an orientation of plies for the composite part, a layer layup rule for the composite part, a layer layup order for the composite part, a description of layer interply for the composite part, and an overall geometry for the composite part.

* * * * *